United States Patent [19]
Zastrow et al.

[11] Patent Number: 5,885,564
[45] Date of Patent: Mar. 23, 1999

[54] FUNCTIONAL OXYGENATED COMPOSITION CONTAINING PHOSPHOLIPIDS AND FLUOROCARBON

[75] Inventors: Leonhard Zastrow; Karin Golz, both of Monaco, Monaco; Klaus Stanzl, White Plains, N.Y.

[73] Assignee: Lancaster Group GmbH, Ludwigshafen, Germany

[21] Appl. No.: 877,040

[22] Filed: Jun. 17, 1997

Related U.S. Application Data

[63] Continuation-in-part of Ser. No. 596,095, filed as PCT/DE94/00943, Aug. 12, 1994, abandoned.

[30] Foreign Application Priority Data

Aug. 13, 1993 [DE] Germany .......................... 43 27 679.2

[51] Int. Cl.⁶ .......................... A61K 9/133; A61K 35/72; A61K 35/74
[52] U.S. Cl. .................... 424/74; 424/78.02; 424/78.03; 424/93 D; 424/93 U; 424/93 S
[58] Field of Search .......................... 424/450, 74, 78.02, 424/78.03, 93 D, 93 U, 93 S

[56] References Cited

U.S. PATENT DOCUMENTS

| | | | |
|---|---|---|---|
| 4,861,593 | 8/1989 | Spearmon et al. | 424/74 |
| 5,015,474 | 5/1991 | Parnell | 424/195.1 |
| 5,466,455 | 11/1995 | Huffstuttler, Jr. | 424/401 |
| 5,576,064 | 11/1996 | Fructus | 424/401 |

FOREIGN PATENT DOCUMENTS 4127442  2/1993  Germany .

*Primary Examiner*—Peter F. Kulkosky
*Attorney, Agent, or Firm*—Collard & Roe, P.C.

[57] ABSTRACT

A composition contains certain nutrients, active and protective substances, as well as an oxygen carrier, along with a process for preparing this composition and its use. The composition provides skin care preparation with a high oxygen content which also contain further nutrients, active and/or protective substances. The new functional oxygenated composition contains (a) phospholipids and oxygen-loaded fluorocarbon or fluorocarbon mixtures. The proportion of fluorocarbon lies in the 0.2 to 100% by weight/volume range. The lipid fraction contains 30 to 99% by weight phosphatidylcholine in the form of asymmetric lamellar aggregates. The composition also contains (b) a product obtained by gentle disintegration of suspensions or dispersions of cells of plant substances, bacteria or yeasts by ultrasonic and/or high-pressure homogenization under up to 25 MPa; and (c) a cosmetic or dermatological carrier suitable for use on the skin. This composition is based for its oxygen content on the synergy between fluorocarbons and the disintegration products.

29 Claims, No Drawings

FUNCTIONAL OXYGENATED COMPOSITION CONTAINING PHOSPHOLIPIDS AND FLUOROCARBON

CROSS REFERENCE TO RELATED PATENT APPLICATION

This patent application is a continuation-in-part of U.S. patent application Ser. No. 08/596,095, filed May 7, 1996, which is a 371 of PCT/DE 94/00943, filed Aug. 12, 1994.

BACKGROUND OF THE INVENTION

1. Field of the Invention

The present invention relates to a preparation which contains nutrient, active and protective substances as well as an oxygen carrier. It furthermore relates to a process for the manufacture of such preparation and its use.

2. The Prior Art

It is known to prepare certain active substances from plants or even from yeasts and to employ these in cosmetics or dermatology. Included therein are inter alia proteins such as peroxide dismutase as described in DE-OS 2,417,509, and EP-A-19,474. It has also already been proposed to encapsulate active substances of vegetable origin in liposome structures and to apply these to the skin.

Furthermore, cosmetic and dermatological products have recently been proposed which, with the aid of phospholipids having high phosphatidylcholine contents and fluorocarbons form novel asymmetrical lamellar structures and due to their good penetration properties are capable of introducing high oxygen contents into the upper skin layers. Fluorocarbons are synthetic products, the manufacture of which, involves considerable costs and which for improved efficacy may be present in cosmetic preparations in amounts of 10% to 40%.

SUMMARY OF THE INVENTION

It is therefore an object of the present invention to provide skin preparations which not only have a high oxygen content but which also have a content of further nutrient, active and/or protective agents with simultaneous cost reductions.

The above object is achieved according to the invention by a functional oxygenaceous preparation comprising, a content of from 0.1% to 50% by weight of phospholipids and an oxygen laden fluorocarbon or fluorocarbon mixture, the proportion of fluorocarbon with reference to the fluorocarbon emulsion produced, being in the range of 0.2% to 100% weight/volume, and comprising a phosphatidylcholine content of the lipid fraction of 30% to 99% by weight in the form of asymmetrical lamellar aggregates, having a skin penetration which is a function of the critical solubility temperature of the fluorocarbons; (b) from 0.1% to 50% by weight of a digestive treatment product obtained by the mild digestive treatment by means of ultrasonic or high pressure homogenization up to 25 MPa or both methods, of suspensions or dispersions of cells of vegetable matter, bacteria or yeasts, which give by the mild digestive treatment proteins, peroxide dismutase, enzymes, nucleic acids, vitamins, fluoroanoides, hormones; and (c) the balance up to 100% by weight of cosmetic or dermatological carrier substances suitable for application to the skin; and with each percent by weight based upon the total preparation weight.

The present invention also provides a process for the manufacture of a functional oxygenaceous preparation, comprising the steps of (a) treating suspensions of dispersions of cells of vegetable matter, bacteria or yeasts digestively by mild ultrasonic treatment or high pressure homogenization up to 25 MPa, or both methods to produce a digestive treatment product of proteins, peroxide dismutase, enzymes, nucleic acids, vitamins, fluoranoides, and hormones; (b) emulsifying phospholipids with an oxygen-laden fluorocarbon or fluorocarbon mixture in an aqueous medium, the fluorocarbon content with reference to the fluorocarbon emulsion produced being in the range of 0.2% to 100% weight/volume and the content in the phosphatidylcholine in the lipid fraction amounting to 30 to 99% by weight; (c) mixing the digestive treatment product of (a) with the emulsion of (b) to produce asymmetrical lamellar aggregates and; (d) incorporating the asymmetrical lamellar aggregates obtained by (c) which incorporate the digestive treatment product of (a) in cosmetic or dermatologic carrier substances suitable for application to the skin; said asymmetrical lamellar aggregates being from 0.1% to 50% by weight of the preparation; said digestive treatment product being from 0.1% to 50% by weight of the preparation; and said carrier being the balance up to 100% by weight; with all percents by weight being based upon the total preparation weight.

The present invention further provides a cosmetic or dermatological functional oxygenaceous preparation, comprising (a) from 0.1% to 50% by weight of phospholipids and an oxygen laden fluorocarbon or fluorocarbon mixture, the proportion of fluorocarbon being in the range of 0.2% to 100% weight/volume, and comprising a phosphatidylcholine content of the lipid fraction of 30% to 99% by weight in the form of asymmetrical lamellar aggregates; (b) from 0.1% to 50% by weight of a digestive treatment product obtained by the mild digestive treatment by means of ultrasonic or high pressure homogenization up to 25 MPa or both methods, of suspensions or dispersions of cells of vegetable matter, bacteria or yeasts, which give by the mild digestive treatment proteins, peroxide dismutase, enzymes, nucleic acids, vitamins, fluoroanoides, hormones; and (c) the balance up to 100% by weight of a cosmetic or dermatological carrier substance suitable for application to the skin for the simultaneous supply of the skin with oxygen and with at least one substance selected from the group consisting of nutrients, active substances, protective agents and pharmaceutically active substances for the skin and the tissue underneath the skin; with all percents by weight being based upon the total preparation weight.

The range of 0.1 to 50% by weight is selected according to the invention as follows. Below 0.1% by weight the effect is not sufficient. If more than 50% by weight are present, the emulsion stability is more difficult to control and the increase in the oxygen content is not so significant.

In the preparation and the process according to the present invention, the fluorocarbon aggregates of (a) preferably range from 0.5% to 45% by weight; the digestive treatment product of (b) preferably ranges from 0.5% to 40% by weight; and the balance up to 100% by weight is the carrier substance of (c).

In the preparations and the process according to the present invention, the fluorocarbon aggregates of (a) more preferably range from 10% to 40% by weight; the digestive treatment product of (b) more preferably ranges from 1% to 10% by weight; and the balance up to 100% by weight is the carrier substance of (c).

It was found that there is a simultaneous presence of asymmetrical lamellar aggregates of fluorocarbons and phospholipids having a high phosphatidylcholine content on the one hand and, on the other hand, of digestive treatment products of cells of vegetable matter or yeasts carried by these aggregates. It was then surprisingly found that there is an amount of oxygen present in the aggregates which is higher than can be expected from the fluorocarbon content and the critical solubility temperature which can be set up therewith. This synergistic effect permits a reduction of the fluorocarbon content with a simultaneous introduction of useful nutritious, active and protective substances derived from the treatment of the vegetable and yeast cells.

Advantageously, green algae, seeds, grains, barks, and plant extracts are employed in the preparation, serving as vegetable substances. During the mild digestive treatment of the cells of these vegetable substances, proteins, enzymes, nucleic acids, vitamins, hormones, fluoranoids, flavonoids, etc., are formed. A particularly advantageous vegetable substance for the preparation according to the invention is the bark of the Mexican Skin tree (Mimosa tenuiflora). The derivative products of this bark have not yet been fully identified. However, when they are used in combination with fluorocarbons or fluorocarbon mixtures, they generate surprisingly high oxygen contents and anti-inflammatory effects in a preparation.

Also particularly valuable embodiments are those combinations in which high proportions of acids, selected from acids such as fruit acids, e.g. malic acid, citric acid, tartaric acid, fumaric acid, succinic acid, gluconic acid as well as lactic acid are used. These acids are processed with fluorocarbons to form preparations which can be applied to the skin.

Likewise valuable embodiments are combinations with vitamins such as one or more of the group comprising vitamin A, vitamin B, vitamin C, vitamin D, vitamin E, vitamin P as well as flavonoids, i.e. the pharmacologically active glycosides of the flavones. These include in particular also the bioflavonoids which are also known as vitamin-P factors, e.g. rutin. Other flavonoids include, for example flavonol, chrysin, galangin, apigenin, fisetin, luteolin, kaempferol, quercetin, morin and their derivatives in the form of biologically active substances.

According to the invention, particularly active preparations also include those which in addition to the elevated oxygen content contain active substances in the form of vitamins comprising the vitamin combinations of P-B-A or A-E-C or B-E-A.

Yeasts which are particularly suitable for the preparation are bakers' yeast, brewers' yeast, wine yeast, as well as yeast enriched with peroxide dismutase.

Bacteria, which are particularly suitable for the preparation are those of the class Pycomycetes such as *Phytophthora cactorum*, Ascomycetes such as *Asperillus niger* K1, *Chaetomium globosum*, and *Penicillinum chrysogenum*. Further examples include Basidomycetes such as *Coniophora cerebella, Corticium confluens*; and also include Deuteromycetes such as *Gloeosporium fructigenum, Fusarium oxysporum, Alternaria solani*, etc.

In the production of the asymmetric lamellar aggregates a large number of fluorocarbons can be employed. Examples of these fluorocarbons include aliphatic straight chain fluoroalkanes and aliphatic branched chain fluoroalkanes, monocyclic fluorocycloalkanes or bicyclic fluorocycloalkanes and optionally fluoroalkyl substituted fluorocycloalkanes, perfluorinated aliphatic amines or perfluorinated bicyclic amines, bis-(perfluoroalkyl)-ethenes, perfluoropolyethers or the mixtures of these fluorocarbons. Those fluorocarbons such as perfluorodecalin, F-butyltetrahydrofuran, perfluorotributylamine, perfluorooctylbromide, bis-fluoro (butyl)ethene or bis-fluoro(hexyl)ethene or $C_6$ to $C_9$ perfluoroalkanes or the mixtures thereof are particularly preferred. In this context, the proportion of fluorocarbons is in the range of 20% to 100% w/v, and preferably in the range of 40% to 100%. A particularly preferred range is that of 70% to 100% w/v.

The term "fluorocarbons" as used herein denotes perfluorinated or highly fluorinated carbon compounds or mixtures which are capable of transporting gases such as $O_2$ and $CO_2$. Highly fluorinated hydrocarbon compounds within the meaning of the invention are those in which most hydrogen atoms have been substituted by fluorine atoms so that a higher degree of substitution does not necessarily increase the gas transporting ability. This is usually attained in those cases where about up to 90% of the hydrogen atoms have been substituted by fluorine atoms. Within the context of the present invention, fluorocarbons are preferred in which at least 95% of the hydrogen atoms have been substituted, preferably 98% and most preferably 100%, by fluorine atoms.

Natural phospholipids such as soyalecithin and egglecithin, synthetic phospholipides as well as hydrogenated lecithines, e.g. phosphorlipone H or partly hydrogenated phospholipids are employed as the phospholipids. In these phospholipids, the content of phosphatidylcholine is in the range of 30% to 99% by weight and in particular in the range of 70% to 90% by weight. Besides phosphatidylcholine, there may also be present lysolecithine in the concentration range of 0.1% to 10% by weight and/or charged phospholipids such as phosphatidylethanolamine, n-acetylphosphatidylethanolamine or phosphatide acid in a concentration range of 0.1% to 30% by weight.

These phospholipid-stabilized aggregates, in contrast to the known aqueous liposomes (vesicles) carry in their nucleus hydrophobic fluorocarbons which have the ability to transport oxygen. Their interfacial chemical stabilization takes place primarily by way of a mono-layer with inverse structure and this may be followed by a build up of bi-layer strata. Because of the peculiarities of their structural arrangement, these novel aggregates are referred to as asymmetric lamellar oxygen carriers. Their unusual colloid chemical stability is presumably derived from the lamellar structure and the surface charges of the aggregates. The latter is caused by the selection of suitable phospholipids or their mixtures of natural as well as synthetic character. Advantageously, phospholipids, in particular phosphatidylcholine in the aforesaid concentration range of 30% to 99% in conjunction with lysolecithins at a concentration of 0.1% to 10% and/or charged phospholipids in the concentration range 0.1% to 30 weight % are primarily responsible. The effect of the phospholipids under discussion is verified by corresponding negative zeta potentials and by the measurement of charge densities (by titration with a cationic polyelectrolyte). An important criterion for the employment of the fluorocarbon aggregates is their skin penetration as a function of the critical solubility temperature of the selected fluorocarbons or fluorocarbon mixtures as described in DE-A-42 21 255.

It is also possible to employ an aqueous fluorocarbon emulsion having a content of 1 to 8 weight % of a non-ionogenic tenside as emulsifier. A particularly advantageous content of fluorocarbons is in the range of 40% to 100% (w/v), and in particular 70% to 100%. Perfluorinated imino-bis (polyoxyalkylenes), polyoxyethylene polyoxypropylene copolymers, ethoxylated sorbitol fatty acid esters, non-ionogenic ethoxylated fluorotensides and/or ethoxylated polypropyleneglycols may be employed as the non-ionogenic tenside.

A particularly advantageous digestive treatment product is obtained by an ultrasonic digestive treatment using an ultrasonic continuous flow cell in which the synotrode projects from ½ to ⅔ of its length into the continuous flow cell. The angle of the synotrode in the sound exposure vessel is in the range of 80.5 to 88.5°. The ratio of immersion length of the synotrode (in mm) to the sound irradiated volume (in ml) is set to a value in the range of 1:1.1 to 1:20. The ratio of immersion length of the synotrode (in mm) to the solids content of the medium to be irradiated with ultrasonic (in weight %) is in the range of 0:0.02 to 1:2.2.

The surprising effect of the combination of asymmetrical lamellar aggregates and the digestive treatments products of vegetable and yeast cells is particularly impressive when treating peroxide dismutase enriched yeasts. These yeasts provide a high content of peroxide dismutase (SOD). Since SOD acts in the skin as a radical capturing agent and catalyses the reaction $$2 O_2^- + 2 H^+ \rightarrow H_2O_2 + O_2$$

it is per se a particularly advantageous component in cosmetic or dermatological preparations. However, other radical capturing agents may be used as well, which are suitable for binding free oxygen radicals, for example vitamin E and P.

A further advantageous preparation comprises the feature that the vegetable digestive treatment product is produced from cells of the Mexican skin tree, whereby a particularly anti-inflammatory oxygen-rich product is obtained.

The invention also relates to a process for the manufacture of the functional oxygenaceous preparation, as discussed above. In this context, the fluorocarbon mixture may also be a fluorocarbon emulsion with non-ionogenic tensides as explained above.

It is particularly advantageous to carry out the cell digestive treatment ultrasonically according to the process described in DE patent application 4,241,154.8. This process, due to the special arrangement of the synotrode in an ultrasonic continuous flow cell, results in an economical and mild digestive treatment of the cells. Also it provides for optimal yields of useful digestion products such as proteins, vitamins, enzymes, etc. In this process, solids concentrations may be present in the medium to be subjected to ultrasonic treatment in the range of 0.5 to 65 weight %. A particularly advantageous synotrode angle amounts to 85.5°. The amplitude is preferably in the range of 20 to 70.

A further possibility for the digestive treatment of the cells resides in high pressure homogenization which can be conducted with pressure applications of up to 25 MPa (about 250 atmospheres). It is also possible in special cases to combine both procedures.

The invention also relates to the use of the functional oxygenaceous preparations including the active substances as described above. These preparations simultaneously supply the skin with high oxygen contents and with one or more substances selected from the group comprising nutrients, active substances, protective agents and pharmaceutically-active substances. These substances may have an effect on the skin and/or the tissue underneath the skin.

Appropriate preparations may be formulated with a carrier as used for cosmetic or dermatological purposes to form ointments, creams, lotions, aqueous solutions, alcoholic extracts, pastes, powders, gels, or tinctures, etc. They may also be used to form skin-care agents, sun protection formulations with UV absorbers, tanning agents, fat replenishing aftershaves, cleansing lotions and oils, or encapsulated radical capturing agents. They can also be used to prepare formulations against pregnancy stretch marks, hair and scalp care agents, bath oils, fitness friction agents, etc.

For this purpose, further pharmaceutical active substances may optionally be included within the formulation. These include, for example, pharmacological active substances in the form of dermatological systemic active substances, including cytostatics, cancerostatics, immunomodulators and vaccines. Particular examples include those of the following group: dermatological active substances such as, for example, virostatics or virocidal medications, antimykotics, heparines (e.g. calcium heparin, sodium heparin, low molecular weight heparines), antibiotics, corticoides, anti-infectives, anti-acne agents, local anesthetics, antiphlogistics, antihistamines or antipsoriatics. Further examples include systemic active agents such as, for example, non-steroidal analgesics/antirheumatics (e.g. sodium, diclofenac, diclofenac diethylamine salt, etofenamate, flufenamine acid, 2-hydroxyethylsalicylate, ibuprofene, indomethacine, piroxicam), opiatereceptoragonists and -antagonists (e.g. buprenorphine, fentanyl pentazocin, pethidin, tilidin, tramadol, naloxone), histamine antagonists (e.g. bamipinlactate, chlorophenoxamine-HCl, clemastinhydrogenfumarate, dimetindenmaleate, pheniraminehydrogenmaleate). Other examples include insulins, regulatory peptides and their inhibitors (e.g. adenohypophyse hormones and their inhibitors, neurohypophyse hormones, hypothalamus hormones), sedatives/hypnotics (e.g. disazepam); and active substances of the group comprising cytostatics, cancerostatics, immunemodulators, and vaccines.

A preferred dermatological active substance is, for example, rosemarine acid or another virucide or a virustatic active substance occurring in plants. A preferred systemic active substance is, for example, a low molecular weight heparin, or high molecular weight heparin, an oligopeptide or a polypeptide.

Further preferred active substances are vitamins (such as E, A, B, C), muramylpeptides, doxorubicin, gentamycin, gramicidin, dexamethasone, hydrocortisone, progesterone, prednisolone as well as their addition salts of acids or bases.

If necessary, one or more antioxidants may be added to the above mentioned dermatological antioxidants.

Preservatives such as parabens (methylparaben or propylparaben), bronopol and biosol may be added to the composition in a range from 0.1% to 1.0% by weight.

Other objects and features of the present invention will become apparent from the following Examples, which disclose the embodiments of the present invention. It should be understood, however, that the Examples are designed for the purpose of illustration only and not as a definition of the limits of the invention.

EXAMPLE 1

Procuction of Fluorocarbon Emulsion 50 ml of a 10% aqueous phospholipid solution (soyalecithin, 40% phosphatidylcholin (PC)) was homogenized jointly with 80 g of a high purity fluorocarbon mixture containing no H atoms (90% perfluorodecalin, 10% F-dibutylmethylamine, critical solubility temperature 26° C.). This was done with an ultrasonic disintegrator and application of ice cooling until the particle size of the particles has attained an average diameter of 244 nm. From $^{31}$P-NMR measurements, the lamellar structure of the aggregates of fluorocarbon and phospholipids is apparent as well as by virtue of the typical signal width from electron-micrographs.

The aggregate dispersion can be mixed without problems and without effecting its stability with suitable alcohols (ethanol, propyleneglycol, glycerol) for purposes of sterilizing. An addition of 30 ml ethanol induces sterility, whereafter the resultant dispersion has the following composition:

| 62 | % w/v fluorocarbons |
|---|---|
| 9.7 | wt. % phospholipids |
| 19 | wt. % ethanol |

The zeta potential of minus 61 mV demonstrates a negative surface charge generated by the phospholipids resulting in an electrostatic stabilization of the dispersion.

Production of the Digestion Product of Yeasts

| 23.5 | weight % backers' yeast |
|---|---|
| 10.0 | weight % glycerin |
| 5.5 | weight % propyleneglycol |
| q.s. | distilled water. |

The distilled water is first introduced at 5° to 7° C. into a container. The yeast is dispersed therein with agitation. Thereafter the glycerin and propyleneglycol are added to the suspension.

The homogeneous yeast suspension is passed by means of a pump through an ultrasonic continuous flow apparatus and is subjected there to ultrasonic treatment. This results in a mild cell digestion and the recovery of the active cellular ingredients (e.g. proteins such as Zn+Cu-peroxide dismutase; vitamins such as vitamin-B complex, vitamin A, and vitamin E).

The parameters in the cell were the following:

| amplitude | 55 |
|---|---|
| synotrode angle | 85.3° |
| through flow velocity | 1 l/h |
| overall volume of the continuous flow vessel | 550 ml |
| length of synotrode in vessel | 30 mm |
| solids content | 23.5 weight % |
| digestion rate | 95–99% |

The ratio of synotrode length:volume:solids content amounted to 1:18:0.8. The overall length of the synotrode was 50 mm. The ratio of synotrode length in the vessel to the overall length therefore amounted to 0.6.

The Production of the Cosmetic Preparation

The digested yeast suspension was centrifuged. 30% of the centrifugate entered into the fluorocarbon aggregates. The combination was added as an active substance complex to the O/W emulsion. All percents are by weight based upon the total weight of the preparation.

O/W Emulsion

Phase A:

| glycerylstearate | 3.5% |
|---|---|
| stearic acid | 2.0% |
| cetylalcohol | 2.0% |
| dimenthinocon | 1.5% |

Phase B:

| distilled water | q.s. |
|---|---|
| Carbomer ® | 0.7% |
| proplyleneglycol | 3.0% |
| preservative | 0.5% |

Phase C:

| active substance complex with digested yeast | 10.0% |
|---|---|

The phases A and B were separately heated to 75° C. and mixed homogeneously. At less than 40° C. the Phase C active substance complex was added with agitation.

EXAMPLE 2

Instead of the yeast digestion product according to Example 1, a digestion product of the bark of the Mexican skin tree was produced having the following composition:

35 weight % skin tree, pulverized
5.0 weight % glycerin
5.0 weight % propyleneglycol
q.s. distilled water.

The processing took place at 15% utilizing a procedure similar to that described above in Example 1. In doing so, the synotrode angle was set to 87.0°, the amplitude was set to 65, the synotrode length in the vessel was set to 33.2 mm and the volume of the throughflow vessel amounted to 650 ml at a throughflow velocity of 0.5 l/h. A digestion rate of 96% was attained for a solids component input of 35 weight %. The ratio of synotrode length:volume:solids content amounted to 1:19:1. At the same synotrode length as in Example 1, the ratio of the synotrode length in the vessel to overall length was 0.644.

The asymmetrical lamellar aggregates, on the basis of perfluorodecalin were mixed in the following manner with this digestion product to form a cosmetic preparation. 30% of the centrifugate entered into the fluorocarbon aggregates and were mixed into the O/W emulsion under the same conditions as in Example 1.

Furthermore, a yeast digestion product was mixed into the preparation to result in a mixture in the ratio of yeast in the fluorocarbon aggregate: Mexican skin tree in fluorocarbon aggregate equal to 2:1.

From the following Table 1, the $O_2$-content in the O/W emulsion after the addition of the active substance components is apparent.

TABLE 1

| | Oxygen Content at 20° C./ppm | | |
|---|---|---|---|
| Product | Immediately after Production | after 24 h | after 4 weeks |
| O/W base (according to example) without active substances | 15.5 | 15.9 | 15.0 |
| O/W (according to example) with fluorocarbon aggregate 25% | 65.6 | 65.0 | 64.9 |
| O/W (according to example) with 10% digested yeast centrifugate | 17.9 | 18.2 | 18.5 |
| O/W (according to example) with 10% of active substance combination; fluorocarbon aggregate + 10% digested yeast centrifugate | 62.5 | 65.0 | 66.2 |

TABLE 1-continued

| | Oxygen Content at 20° C./ppm | | |
|---|---|---|---|
| Product | Immediately after Production | after 24 h | after 4 weeks |
| O/W (according to example) with 10% of active substance combination; fluorocarbon aggregate + 10% digested Mexican skin tree centrifugate | 18.0 | 17.8 | 17.6 |
| O/W (according to example) with 10% of active substance combination; fluorocarbon aggregate and digested yeast/ Skin tree centrifugate in a ratio 2:1 - 10% | 65.8 | 79.5 | 79.9 |

From table 1, it is clearly apparent that even 10% of fluorocarbon aggregate and 10% digestion product of the Mexican skin tree result in a clear increase of the oxygen content to a value which is close to that of a 25% content of fluorocarbon aggregate. This is clear proof for the synergistic effect which is also supported by the 2:1 mixture of yeast and Skin tree centrifugate.

EXAMPLES 3 TO 6

The following Examples 3 to 6 show further results of $O_2$ measurements with different amounts of digestion products and fluorocarbon aggregates (based on perfluorodecalin) (Table 2).

TABLE 2

| | | | $O_2$ at 20° C. [ppm] | | |
|---|---|---|---|---|---|
| Ex. No. | Ingredients | % by weight | immed. after prod. | after 24 h | after 4 wks. |
| 3a | fluorocarbon aggregates | 0.5 | — | 16.9 | 17. |
|  | digestion product of green algae | 0.5 | | | |
| 3b | fluorocarbon aggregates | 0.5 | — | 16.2 | 16.2 |
|  | digestion product of green algae | — | | | |
| 4a | Fluorocarbon aggregates | 0.5 | 29.5 | 31.0 | 32.0 |
|  | digestion product of yeast | 0.5 | | | |
| 4b | Fluorocarbon aggregates | — | 15.3 | 15.5 | 15.5 |
|  | digestion product of yeast | 0.5 | | | |
| 5a | Fluorocarbon aggregates | 0.1 | 20.8 | 21.2 | 22.5 |
|  | digestion product of yeast | 40 | | | |
| 5b | fluorocarbon aggregates | — | 17.1 | 17.3 | 17.5 |
|  | digestion product of yeast | 40 | | | |
| 6a | fluorocarbon aggregates | 40 | 91.7 | 92.0 | 93.2 |
|  | digestion product of yeast | 0.5 | | | |

TABLE 2-continued

| | | | $O_2$ at 20° C. [ppm] | | |
|---|---|---|---|---|---|
| Ex. No. | Ingredients | % by weight | immed. after prod. | after 24 h | after 4 wks. |
| 6b | fluorocarbon aggregates | 40 | 83.9 | 84.0 | 89.0 |
|  | digestion product of yeast | — | | | |

In the following examples 7 to 11, all amounts are in % by weight. The fluorocarbon aggregates are based on perfluorodecalin and the preservative is methylparaben.

EXAMPLE 7

| Face and body emulsion | |
|---|---|
| Phase A | |
| C12-15 Alkyl Benzoate | 3.5 |
| Steareth-2 ® | 3.0 |
| Steareth-21 ® | 1.9 |
| Caprylic/Capric Triglyceride PEG-4 Esters | 2.5 |
| Phase B | |
| Distilled water | q.s |
| Acrylate and C10-C30 Alkyl Acrylate Crosspolymer | 0.4 |
| Phase C | |
| Triethanolamine | 0.4 |
| Phase D | |
| Jojoba oil | 1.5 |
| Babassu oil | 1.0 |
| Vitamin E | 0.5 |
| Preservative | 0.3 |
| Phase E | |
| Fluorocarbon aggregates | 0.1 |
| Yeast extract | 0.1 |
| Perfume | 0.3 |

The phases A and B were separately heated with stirring to 60° C. ±0.2° C. Phase A was added to Phase B and then homogenized well. Phase C was then added. Following the addition of Phase C, there was cooling to 40°–42° C. Then phase D was added during further mixing. Then phase E was mixed with the product after cooling to 35° C.

EXAMPLE 8

| Face and eye cleansing milk | |
|---|---|
| Phase A | |
| Steareth-2 ® | 1.5 |
| Caprylic/Capric Triglyceride PEG-4 Esters | 1.5 |
| Calendula oil | 2.0 |
| Phase B | |
| Distilled water | q.s. |
| Carbomer ® | 0.5 |
| Phase C | |
| Triethanolamine | 0.4 |

Face and eye cleansing milk

| Phase D | |
|---|---|
| Fluorocarbon aggregates | 0.5 |
| Green algae extract | 2.0 |
| Preservative | 0.3 |

The product was prepared utilizing a procedure analogous to that described above for Example 7.

EXAMPLE 9

Anti-wrinkle mask

| Phase A | |
|---|---|
| Cetearyl Alcohol | 2.8 |
| Octyl Stearate | 1.8 |
| Dicaprylyl Ether | 1.0 |
| Phase B | |
| Distilled Water | q.s. |
| Acrylate C10-C30 Alkyl Acrylate Crosspolymer | 0.4 |
| Phase C | |
| Triethanolamine | 0.4 |
| Phase D | |
| Kaolin modified acc. to WO96/17588 | 5.6 |
| Vitamin E | 1.2 |
| Preservative | 0.4 |
| Babassu oil | 2.0 |
| Palm oil | 1.0 |
| Phase E | |
| Fluorocarbon aggregates | 45.0 |
| Yeast extract | 10.0 |
| Perfume oil | 0.3 |

The product was prepared utilizing a procedure analogous to that described above for Example 7.

EXAMPLE 10

Heparin ointment

| Distilled water | q.s. |
|---|---|
| Heparin | 1.0 |
| Carbomer ® | 2.0 |
| Sodium hydroxide | 2.0 |
| Phospholipid (Lecithin) | 9.0 |
| Perfluorodecalin | 20 |
| Fluorocarbon aggregates | 7.0 |
| Yeast extract | 2.0 |
| Preservative | 0.1 |

The heparin and the fluorocarbon aggregates were added to perfluorodecalin under vigorous mixing. The temperature was maintained at or below 35° C. After that, the other ingredients were added in the manner described above.

The $O_2$ content at 20° C. was measured immediately after preparation and was found to be 75.8 ppm; after 24 hours the oxygen content was found to be 75.9 ppm, and after 4 weeks the oxygen content was found to be 80.1 ppm. EXAMPLE 11

Ointment with Acetylsalicylic acid

| Distilled water | q.s. |
|---|---|
| Acetylsalicylic acid (ASA) | 1.0 |
| Glycerin | 8.0 |
| Propylene glycol | 6.0 |
| Ethanol | 1.0 |
| Phospholipid (Lecithin) | 4.5 |
| Fluorocarbon aggregates | 40.0 |
| Yeast extract | 1.0 |

The product was prepared utilizing a procedure analogous to that described in Example 10, except for the addition of perfluorodecalin.

Accordingly, while only several embodiments of the present invention have been shown and described, it is obvious that many changes and modifications may be made thereunto without departing from the spirit and scope of the invention.

What is claimed is:

1. Functional oxygenaceous preparation, comprising a content of
   (a) from 0.1% to 50% by weight of phospholipids and an oxygen laden fluorocarbon or fluorocarbon mixture, which is emulsified to produce a fluorocarbon emulsion, said fluorocarbon content being in the range of 0.2% to 100% weight/volume of said emulsion, and comprising a lipid fraction having a phosphatidylcholine content of 30% to 99% by weight, said emulsion and said lipid fraction forming asymmetrical lamellar aggregates, having a skin penetration which is a function of the critical solubility temperature of the fluorocarbon;
   wherein the fluorocarbon is selected from the group consisting of aliphatic straight chain fluoroalkanes, branched chain fluoroalkanes, monocylic fluorocycloalkanes, bicyclic fluorocycloalkanes, optionally fluoroalkyl substituted fluorocycloalkanes, perfluorinated aliphatic amines, perfluorinated bicylic amines, bis-(perfluoroalkyl)-ethenes, and the mixtures thereof;
   (b) from 0.1% to 50% by weight of a digestive treatment product obtained by a mild digestive treatment by means of ultrasonic or high pressure homogenization up to 25 MPa or both methods, of suspensions or dispersions of cells selected from the group consisting of vegetable matter, bacteria and yeasts, said product selected from the group consisting of proteins, peroxide dismutase, enzymes, nucleic acids, vitamins, fluoroanoides, and hormones; and
   (c) the balance up to 100% by weight of a carrier substance suitable for application to the skin; and
   with each percent by weight based upon the total preparation weight; and
   said preparation having increased oxygen content due to the presence of said digestive treatment product.

2. A preparation according to claim 1, wherein the yeast is selected from the group consisting of bakers' yeast, brewers' yeast, wine yeast, and yeast enriched with peroxide dismutase.

3. A preparation according to claim 1, wherein the vegetable matter is the bark of the Mexican skin tree, (*Mimosa tenuiflora*).

4. A preparation according to claim 1, wherein the vegetable matter is selected from the group consisting of green algae, seeds, grains, barks, and plant extracts.

5. A preparation according to claim 1,
wherein the digestive treatment product further contains at least one substance selected from the group consisting of proteins, Aloe vera, rosemarine, and camomile.

6. A preparation according to claim 1,
wherein the digestive treatment product further contains a combination of fruit acids selected from the group consisting of malic acid, citric acid, tartaric acid, fumaric acid, succinic acid, gluconic acid, and lactic acid.

7. A preparation according to claim 1,
wherein the digestive treatment product further contains vitamins comprising the vitamin combinations selected from the group consisting of P-B-A, A-E-C, and B-E-A.

8. A preparation according to claim 1,
wherein the fluorocarbons are selected from the group consisting of perfluorodecalin, F-butyltetrahydrofuran, perfluorotributylamine, perfluorooctylbromide, bis-fluoro (butyl) ethene and $C_6$-$C_9$-perfluoroalkanes, and the mixtures thereof.

9. A preparation according to claim 1,
wherein the proportion of fluorocarbons is in the range of 20% to 100% w/v, in the fluorocarbon emulsion, which is added to the lipid fraction.

10. A preparation according to claim 1,
wherein the proportion of fluorocarbons is in the range of 40% to 100% w/v, in the fluorocarbon emulsion which is added to the lipid fraction.

11. A preparation according to claim 1,
wherein the fluorocarbon aggregates of (a) range from 0.5% to 45% by weight;
wherein the digestive treatment product of (b) range from 0.5% to 40% by weight; and
the balance up to 100% by weight is the carrier substance of (c).

12. A preparation according to claim 1,
wherein the fluorocarbon aggregates of (a) range from 10% to 40% by weight;
wherein the digestive treatment product of (b) range from 1% to 10% by weight; and
the balance up to 100% is the carrier substance of (c).

13. Process for the manufacture of a functional oxygenaceous preparation, comprising the steps of
(a) treating suspensions of dispersions of cells of vegetable matter, bacteria or yeasts digestively by mild ultrasonic treatment or high pressure homogenization up to 25 MPa, or both methods to produce a digestive treatment product selected from the group consisting of proteins, peroxide dismutase, enzymes, nucleic acids, vitamins, fluoranoides, and hormones;
(b) emulsifying a lipid fraction containing phospholipids with an oxygen-laden fluorocarbon emulsion comprising a fluorocarbon or fluorocarbon mixture in an aqueous medium, the fluorocarbon content in the fluorocarbon emulsion being in the range of 0.2% to 100% weight/volume and the content of phosphatidylcholine in the lipid fraction amounting to 30% to 99t by weight;
wherein the fluorocarbon is selected from the group consisting of aliphatic straight chain fluoroalkanes, branched chain fluoroalkanes, monocylic fluorocycloalkanes, bicyclic fluorocycloalkanes, optionally fluoroalkyl substituted fluorocycloalkanes, perfluorinated aliphatic amines, perfluorinated bicylic amines, bis-(perfluoroalkyl)-ethenes, and the mixtures thereof;

(c) mixing the digestive treatment product of (a) with the emulsion of (b) to produce asymmetrical lamellar aggregates and;
(d) incorporating the asymmetrical lamellar aggregates obtained by (c) which incorporate the digestive treatment product of (a) in a carrier substance suitable for application to skin;
said asymmetrical lamellar aggregates being from 0.1% to 50% by weight of the preparation;
said digestive treatment product being from 0.1% to 50% by weight of the preparation; and
said carrier being the balance up to 100% by weight;
with all percents by weight being based upon the total preparation weight; and
said preparation having increased oxygen content due to the presence of said digestive treatment product.

14. Process according to claim 13, comprising
obtaining the digestive treatment product by an ultrasonic digestive treatment using an ultrasonic continuous flow cell in which the synotrode projects as to ½ to ⅔ its length into the continuous flow cell, the angle of the synotrode in the sound exposure vessel being in the range of 80.5° to 88.5°, the ratio of immersion length of the synotrode (in mm) to the sound irradiated volume (in ml) being set to a value in the range of 1:1.1 to 1:20 and the ratio of immersion length of the synotrode (in mm) to a solids content of the medium to be irradiated ultrasonically (in weight %) being in the range of 0:0.02 to 1:2.2.

15. Process according to claim 14,
wherein the solids concentration present in the medium to be subjected to ultrasonic treatment is in the range of 0.5 to 65 weight %.

16. Process according to claim 13,
wherein particle size of the asymmetrical lamellar aggregates is in the range of 50 to 1000 nm.

17. Process according to claim 13,
wherein particle size of the asymmetrical lamellar aggregates is in the range of 120 to 820 nm.

18. Process according to claim 13,
wherein particle size of the asymmetrical lamellar aggregates is in the range of 140 to 400 nm.

19. Process according to claim 13,
wherein the fluorocarbon aggregates of (a) range from 0.5% to 45% by weight;
wherein the digestive treatment product of (b) range from 0.5% to 40% by weight; and
the balance up to 100% by weight is the carrier substance of (c).

20. Process according to claim 13,
wherein the fluorocarbon aggregates of (a) range from 10% to 40% by weight;
wherein the digestive treatment product of (b) range from 1% to 10% by weight; and
the balance up to 100% is the carrier substance of (c).

21. A cosmetic or dermatological functional oxygenaceous preparation, comprising
(a) from 0.1% to 50% by weight of phospholipids and an oxygen laden fluorocarbon or fluorocarbon mixture which is emulsified to produce a fluorocarbon emulsion, the proportion of fluorocarbon being in the range of 0.2% to 100% weight/volume of said emulsion, and comprising a lipid fraction having a phosphatidylcholine content of 30% to 99% by weight and said emulsion and said lipid fraction forming asymmetrical lamellar aggregates;

wherein the fluorocarbon is selected from the group consisting of aliphatic straight chain fluoroalkanes, branched chain fluoroalkanes, monocylic fluorocycloalkanes, bicyclic fluorocycloalkanes, optionally fluoroalkyl substituted fluorocycloalkanes, perfluorinated aliphatic amines, perfluorinated bicylic amines, bis-(perfluoroalkyl)-ethenes, and the mixtures thereof;

(b) from 0.1% to 50% by weight of a digestive treatment product obtained by the mild digestive treatment by means of ultrasonic or high pressure homogenization up to 25 MPa or both methods, of suspensions or dispersions of cells of vegetable matter, bacteria or yeasts, said product selected from the group consisting of proteins, peroxide dismutase, enzymes, nucleic acids, vitamins, fluoroanoides, and hormones; and (c) the balance up to 100% by weight of a carrier substance suitable for application to skin for the simultaneous supply of the skin with oxygen and with at least one substance selected from the group consisting of nutrients, active substances, protective agents and pharmaceutically active substances for the skin and the tissue underneath the skin;

with all percents by weight being based upon the total preparation weight; and said preparation having increased oxygen content due to the presence of said digestive treatment product.

22. The cosmetic or dermatological functional oxygenaceous preparation according to claim 21, wherein said substance (c) is selected from the group consisting of skin-care agents, sun protection formulations with UV absorbers, tanning agents, fat replenishing after-shaves, cleansing lotions and oils, encapsulated radical capturing agents, formulations against pregnancy stretch marks, hair and scalp care agents, bath oils, fitness friction agents, dermatological formulations with or without further pharmaceutically active substances.

23. A preparation according to claim 21, wherein the fluorocarbon aggregates of (a) range from 0.5% to 45% by weight;

wherein the digestive treatment product of (b) range from 0.5% to 40% by weight; and the balance up to 100% by weight is the carrier substance of (c).

24. A preparation according to claim 21, wherein the fluorocarbon aggregates of (a) range from 10% to 40% by weight;

wherein the digestive treatment product of (b) range from 1% to 10% by weight; and the balance up to 100% is the carrier substance of (c).

25. A preparation according to claim 21, comprising a face and body emulsion which consists essentially of 3.5% by weight of C12–15 alkyl benzoate;
3.0% by weight of Steareth-2®;
1.9% by weight of Steareth-21®;
2.5% by weight of caprylic/capric triglyceride PEG-4 esters;
q.s. distilled water;
0.4% by weight of acrylates and C10–C30 alkyl acrylate crosspolymer;
0.4% by weight of triethanolamine;
1.5% by weight of Jojoba oil;
1.0% by weight of Babassu oil;
0.5% by weight of Vitamin E;
0.3% by weight of Preservative;
0.1% by weight of fluorocarbon aggregates;
0.1% by weight of yeast extract; and
0.3% by weight of perfume.

26. A preparation according to claim 21, comprising a face and eye cleansing milk which consists essentially of 1.5% by weight of Steareth-2®;
1.5% by weight of caprylic/capric triglyceride PEG-4 esters; 2.0% by weight of Calendula oil;
q.s. distilled water;
0.5% by weight of Carbomer®;
0.4% by weight of triethanolamine;
0.5% by weight of fluorocarbon aggregates;
2.0% by weight of Green algae extract; and
0.3% by weight of preservative.

27. A preparation according to claim 21, comprising an anti-wrinkle mask which consists essentially of 2.8% by weight of cetearyl alcohol;
1.8% by weight of octyl stearate;
1.0% by weight of dicaprylyl ether;
q.s. distilled Water;
0.4% by weight of acrylates and C10–C30 alkyl acrylate crosspolymer;
0.4% by weight of triethanolamine;
5.6% by weight of kaolin;
1.2% by weight of Vitamin E;
0.4% by weight of preservative;
2.0% by weight of Babassu oil;
1.0% by weight of Palm oil;
45.0% by weight of fluorocarbon aggregates;
10.0% by weight of yeast extract; and
0.3% by weight of perfume oil.

28. A preparation according to claim 21, comprising a heparin ointment which consists essentially of q.s. Distilled water;
1.0% by weight of heparin;
2.0% by weight of Carbomer;
2.0% by weight of sodium hydroxide;
9.0% by weight of phospholipid;
20% by weight of perfluorodecalin;
7.0% by weight of fluroocarbon aggregates;
2.0% by weight of yeast extract; and
0.1% by weight of preservative.

29. A preparation according to claim 21, comprising an ointment with acetylsalicylic acid which consists essentially of q.s. distilled water;

1.0% by weight of acetylsalicylic acid;
8.0% by weight of glycerin;
6.0% by weight of propylene glycol;
1.0% by weight of ethanol;
4.5% by weight of phospholipid;
40.0% by weight of fluorocarbon aggregates; and
1.0% by weight of yeast extract.

* * * * *